(12) United States Patent
Kulkarni et al.

(10) Patent No.: US 9,091,597 B2
(45) Date of Patent: Jul. 28, 2015

(54) ELECTRODE-ASSISTED MICROWAVE-INDUCED PLASMA SPECTROSCOPY

(71) Applicant: Centers for Disease Control and Prevention, Atlanta, GA (US)

(72) Inventors: Pramod Kulkarni, Mason, OH (US); Philip Efthimion, Pluckemin, NJ (US)

(73) Assignee: The United States of America, as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 23 days.

(21) Appl. No.: 13/804,512

(22) Filed: Mar. 14, 2013

(65) Prior Publication Data

US 2013/0321804 A1    Dec. 5, 2013

Related U.S. Application Data

(60) Provisional application No. 61/652,593, filed on May 29, 2012.

(51) Int. Cl.
*G01J 3/30* (2006.01)
*G01J 3/443* (2006.01)
(Continued)

(52) U.S. Cl.
CPC ............. *G01J 3/443* (2013.01); *G01N 15/0656* (2013.01); *G01N 21/67* (2013.01); *G01N 21/718* (2013.01)

(58) Field of Classification Search
CPC ..... G01J 3/443; G01N 15/0656; G01N 21/68; G01N 22/00; G01N 21/63

USPC .................................. 356/313, 316; 250/564
See application file for complete search history.

(56) References Cited

U.S. PATENT DOCUMENTS 3,653,766 A    4/1972   Walters et al.
3,736,059 A    5/1973   Schuhknecht et al.
(Continued)

FOREIGN PATENT DOCUMENTS

WO    2010/003613 A1    1/2010
WO    2012/048308 A2    4/2012

OTHER PUBLICATIONS

Prasoon Diwakar, Pramod Kulkarni & M. Eileen Birch, "New Approach for Near-Real-Time Measurement of Elemental Composition of Aerosol Using Laser-Induced Breakdown Spectroscopy", Aerosol Science and Technology, 46:3, 316-332 (2012).

(Continued)

*Primary Examiner* — Tri T Ton
*Assistant Examiner* — Willie Merrell, II
(74) *Attorney, Agent, or Firm* — Gifford, Krass, Sprinkle, Anderson & Citkowski, P.C.; Douglas L. Wathen

(57) ABSTRACT

Particles of a flow of aerosol are collected and analyzed by passing them through a housing having an inlet area, an outlet area, and a collection and analysis area. A collection electrode has a tip disposed in the flow path in the collection and analysis area. Particles are collected on the tip of the collection electrode. A microwave pulse is applied to the collection and analysis area such that a plasma is created. Atomic emissions produced during at least part of the microwave step are collected for analysis of the ablated particles.

14 Claims, 2 Drawing Sheets

(51) Int. Cl.
*G01N 21/71* (2006.01)
*G01N 21/67* (2006.01)
*G01N 15/06* (2006.01)

(56) References Cited

U.S. PATENT DOCUMENTS

| | | | | |
|---|---|---|---|---|
| 3,843,257 | A | * | 10/1974 | Wooten .......................... 356/316 |
| 4,883,570 | A | * | 11/1989 | Efthimion et al. ............ 204/164 |
| 5,153,519 | A | | 10/1992 | Wentworth et al. |
| 5,955,886 | A | * | 9/1999 | Cohen et al. ................... 324/464 |
| 6,012,326 | A | * | 1/2000 | Raybone et al. ............. 73/31.02 |
| 6,081,329 | A | * | 6/2000 | Cohn et al. .................... 356/316 |
| 6,455,850 | B1 | * | 9/2002 | Coates et al. .............. 250/338.1 |
| 7,530,265 | B2 | | 5/2009 | DiFoggio |
| 7,701,578 | B1 | | 4/2010 | Herring |
| 7,862,649 | B2 | | 1/2011 | Sakuma et al. |
| 8,007,566 | B2 | | 8/2011 | Abdelkrim et al. |
| 2008/0055594 | A1 | * | 3/2008 | Hadidi et al. ................. 356/316 |
| 2008/0316139 | A1 | * | 12/2008 | Blaser et al. .................. 343/872 |

OTHER PUBLICATIONS

Prasoon Diwakar, Pramod Kulkarni, Eileen Birch, "Semi-Continuous Measurement of Elemental Composition of Aerosol Particles Using Laser Induced Breakdown Spectroscopy," AAAR 29th Annual Conference, presented by the American Association for Aerosol Research, Abstract only (2010).

Yuji Ikeda et al., "Development of microwave-enhanced spark-induced breakdown spectroscopy," Applied Optics, vol. 49, No. 13 pp. pp. C95-C100 (May 1, 2010).

Yuan Liu et al., "Elemental analysis by microwave-assisted laser-induced breakdown spectroscopy: Evaluation on ceramics," J. Anal. At. Spectrom., 25, pp. 1316-1323 (2010).

\* cited by examiner

FIG. 1

ELECTRODE-ASSISTED MICROWAVE-INDUCED PLASMA SPECTROSCOPY

CROSS REFERENCE TO RELATED APPLICATION

This application claim priority to U.S. provisional patent application Ser. No. 61/652,593, filed May 29, 2012, the entire content of which is incorporated herein in its entirety.

FIELD OF THE INVENTION

The present invention relates generally to methods and apparatus for the collection and analysis of aerosol particles.

BACKGROUND OF THE INVENTION

An aerosol is a suspension of fine solid particles or liquid droplets in a gas. There is a need to analyze the particles of an aerosol especially where the particles of aerosol are unidentified or contain pollutants that must be monitored or limited. There are numerous approaches to provide instruments and methods for the collection and analysis of particles of an aerosol. However, each of these approaches has had certain drawbacks with respect to development of hand-portable instruments and sensors to allow real-time chemical analysis of aerosols with excellent limit of detection. As such, there is a need for improved real-time or semi-continuous methods and apparatus for the collection and analysis of particles of an aerosol. Most current technologies used for real-time chemical analysis of aerosols are not amenable to compact, hand-held instrumentation.

SUMMARY OF THE INVENTION

The present invention provides for collection of airborne particles on a tip of a electrode (approx. several micrometers to several millimeters in diameter), followed by ablation and atomic emission detection of the particulate matter on the tip by a microwave-induced plasma. The present invention provides an apparatus and a method for its use. The overall process of measurement of atomic spectra of aerosols can be divided into three steps: i) Particle collection and preconcentration; ii) Introduction of pulsed microwave-induced plasma; and iii) measuring the ensuing atomic emission and recording the signals.

In one embodiment, particles of a flow of aerosol are collected and analyzed by passing them through a housing having an inlet area, an outlet area, and a collection and analysis area. A collection electrode has a tip disposed in the flow path in the collection and analysis area. Particles are collected on the tip of the collection electrode. A microwave pulse is applied to the collection and analysis area such that a plasma is created. Atomic emissions produced during at least part of the microwave sustained plasma are collected for analysis of the ablated particles. A plurality of other embodiments are also provided.

BRIEF DESCRIPTION OF THE DRAWINGS

FIG. 1 is a schematic of an embodiment of an apparatus for use with the present invention;

FIG. 2 is a cross sectional view of an embodiment of an apparatus in accordance with the present invention;

DETAILED DESCRIPTION OF THE INVENTION

Figure 4:
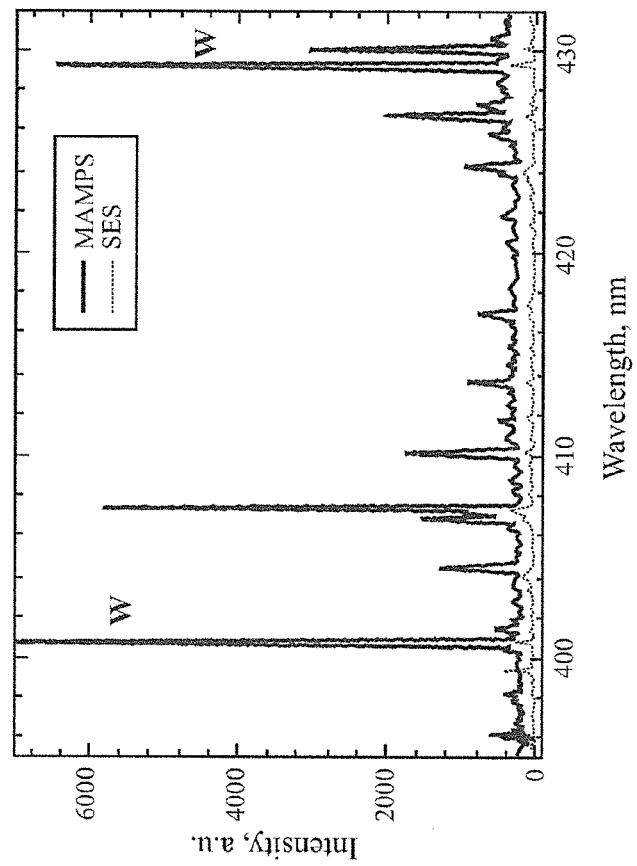
FIG. 4 is a representation of two spectra of tungsten; one obtained using pulsed high-voltage spark plasma and one using microwave plasma in accordance with the present invention.

This invention involves collection of airborne particles on a tip of an electrode (approx. several micrometers to several millimeters in diameter), followed by ablation and atomic emission detection of the particulate matter on the tip by a microwave-induced plasma. The present invention provides an apparatus and a method for its use. The overall process of measurement of atomic spectra of aerosols can be divided into three steps: i) Particle collection and preconcentration; ii) Introduction of pulsed microwave-induced plasma; and iii) measuring the ensuing atomic emission and recording the signals.

Figure 1:
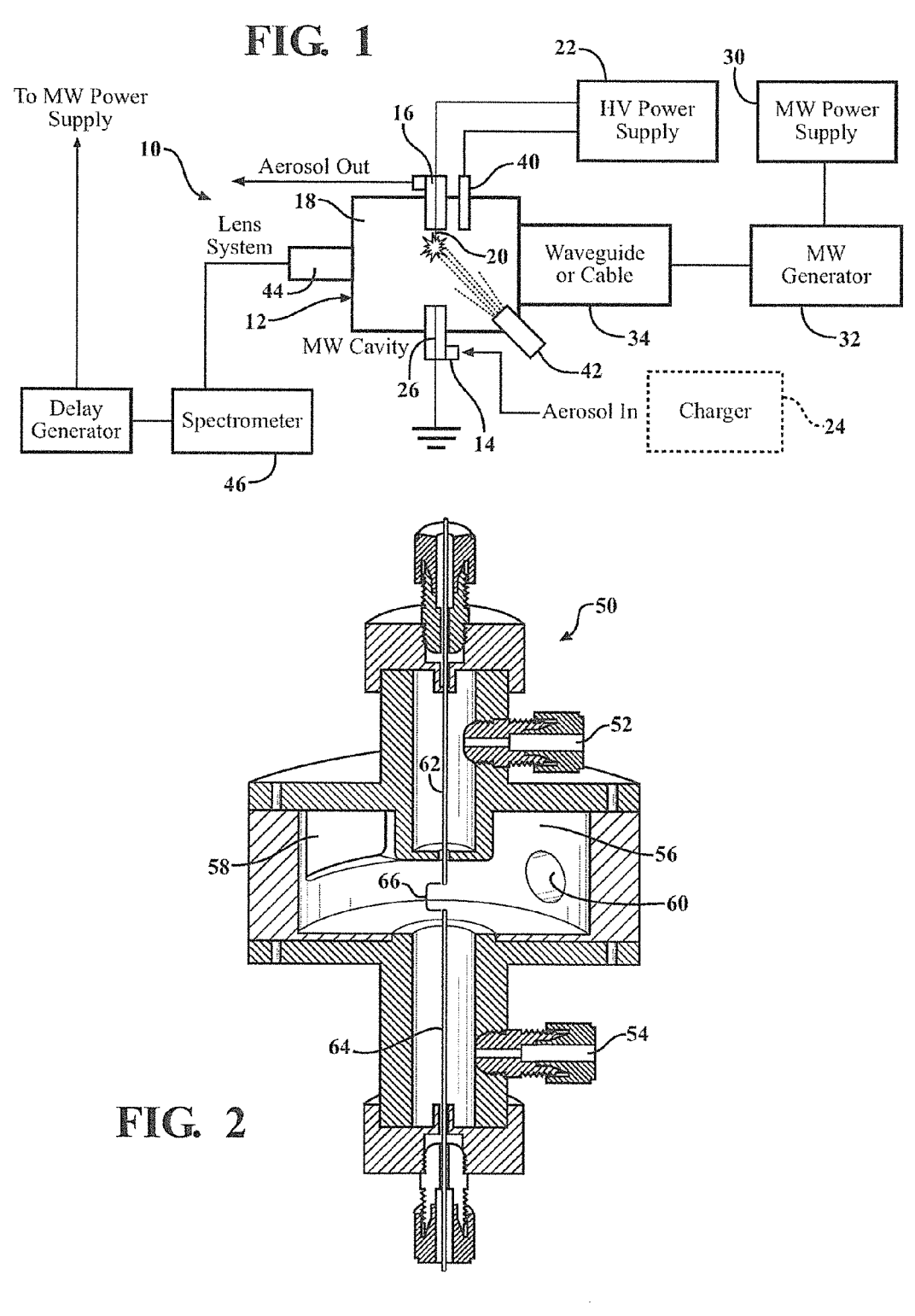

FIG. 1 provides a schematic of an embodiment of an apparatus 10 in accordance with the present invention. The apparatus include a housing 12 with an inlet 14, an outlet 16 and a collection and analysis area 18 interconnecting the inlet and outlet. The collection and analysis area may be in a microwave cavity, such as a reentrant type cavity. Alternatively, any other type of microwave cavity may be used. A flow path may be said to be defined from the inlet 14, through the collection and analysis area 18, and out the outlet 16.

A collection electrode 20 is provided in the collection and analysis area 18. This electrode may also be called a microelectrode. Particles of the aerosol flowing along the flow path are collected on the tip of the electrode 20. This may be done in a number of ways. As shown, a high voltage power supply 22 is connected to the collection electrode 20. In one approach, the aerosol is passed through an optional aerosol charger 24 (to impart electrical charge to the aerosol particles) prior to being introduced into the collection and analysis area 18. The charger may be of any type known to those of skill in the art. The collection electrode 20 may then be held at a bias voltage relative to the charged particles of the aerosol such that charged particles collect on the tip of the electrode 20.

In another approach, a second electrode 26 is provided, which may be coaxially aligned with the collection electrode 20. The second electrode 26 may be connected to a power supply (to apply high potential) or to ground, and the collection electrode 20 may be connected to a power supply or ground. The second electrode 26 maybe provided with a corona current such that an excess of ions are produced around the second electrode. The particles of the aerosol are then charged by these ions. Again, the collection electrode 20 may be held at a bias voltage so as to attract the particles. Alternatively, the second electrode 26 may be held at a second voltage relative to the bias voltage so as to create an electrical field forcing the charged particles toward the collection electrode.

Particles may be collected on the collection electrode in any of a number of other ways (in addition to electrostatic method described above). For example, particle preconcentration on the electrode can be accomplished or assisted via an aerodynamic lens or a focused particle beam using orifices, nozzles, or capillaries. An additional particle-free sheath flow arrangement surrounding the aerosol sample flow can be used to improve particle preconcentration on the electrode 20. Any of these approaches, or combination thereof, may be used with or without an upstream charger 24.

After the particle collecting step, the present invention provides for creating a plasma and collecting the atomic emissions to analyze the particles. In accordance with the present invention, the plasma is created and/or sustained by a pulse of microwave from a microwave source. FIG. 1 schematically illustrates a microwave power supply 30 powering a microwave generator 32. The generator 32 creates the pulse of microwave, which is directed into the collection and analysis area by a waveguide 34 or a cable, such as a coaxial cable. Alternatively, any other type of microwave system may be used.

In one approach, the microwave pulse is applied to the collection and analysis area and the presence of the electrode in the microwave cavity concentrates the electromagnetic field on its tip, subsequently leading to formation of plasma on the tip upon introduction of pulsed microwaves (as one example, f=2.45 GHz, peak power=3 kW may be used). The plasma leads to ablation, atomization, and atomic emission of the particle-bound analyte. The lifetime of the plasma can be changed by changing the duration of the microwave pulses. A plasma lifetime of the order of 5-40 ms can be obtained in this system. The longer lifetime of microwave plasma, compared to laser and spark plasmas, leads to larger atomic emission signals and better sensitivity.

The presence of the electrode in the cavity itself is sufficient to create the plasma on its tip. To further improve the reproducibility of the microwave plasma characteristics, a number of other techniques may be employed, which enhance the concentrations of electrons and ions in the vicinity of the collection electrode to allow efficient reproducible coupling of microwaves.

In a first enhancement approach, a stable, continuous ac or dc corona is introduced on the tip of the collection electrode 20 (on which the particles are collected), which provides additional seed electrons and ions for effective coupling of microwaves. This significantly improves the repeatability and stability of the pulsed microwave plasma. In one configuration, the corona is produced on the second electrode 26 (held at high potential) during the particle collecting step, but during microwave introduction, the corona is created on the tip of the collection electrode 20 by reversing the polarity. Other configurations using different combinations of polarities of high voltage and collection or other electrodes are possible.

In a second enhancement approach, a corona electrode 40 is provided for production of a corona. This corona electrode (or electrodes if multiple are provided) are located very close to the collection electrode 20 (so that a high concentration of electrons is obtained in the vicinity of the collection electrode).

In a third enhancement approach, a bias voltage (high enough to create a microwave discharge but not a corona) is applied to either the collection electrode 20 or the second electrode 26 to create a microwave discharge.

A fourth enhancement approach involves introduction of a pulsed spark or laser plasma, which leads to ablation and atomization of the particulate sample on the collection electrode, followed by immediate introduction of the pulsed microwaves, providing a tandem scheme. This scheme uses the pulsed high-voltage spark or laser plasma to ablate the particulate sample preconcentrated on the electrode, whereas the microwave plasma energy promotes and sustains atomic emissions over an extended period of time. FIG. 1 shows a "source" 42 which may represent a laser aimed at the collection electrode 20. If spark ablation is to be used, a spark may be created between the collection electrode 20 and the second electrode 26 or another electrode.

In a fifth enhancement approach, an alternate source of seed electrons is provided, such as UV or soft X-ray photoionization, to induce ionization of air in the vicinity of the collection electrode 20. Source 42 may represent such a source.

In a sixth enhancement approach, an additional source of ions and electrons, produced in a gas phase outside the cavity, may be brought in into the microwave cavity using a carrier gas flow to allow effective coupling of microwaves, or using small radioactive alpha and beta sources to provide ionized particles.

The next step in practicing the present invention is that the resulting atomic emissions are detected using an optical spectrometer. FIG. 1 shows a lens system 44 and a spectrometer 46 for collecting and analyzing the atomic emissions from the ablated particles.

Referring now to FIG. 2, an exemplary housing for use with the present invention is illustrated. The housing 50 has an inlet 52 and an outlet 54 with a collection and analysis area 56 interconnecting the inlet and outlet. The collection and analysis area in this embodiment is a reentrant type microwave cavity and has a window 58 for introduction of microwave pulses and another window 60 for light collection for the spectrometer. Electrodes 62 and 64 extend into the collection and analysis area 56 and have tips separated by a spark gap 66. The electrodes may be used in any of the ways discussed above, with one acting as a collection electrode and one as a second electrode. The inlet and outlet for the aerosol in this embodiment is to the side, though other arrangements are possible. The electrodes may be arranged other than shown.

Figure 3:
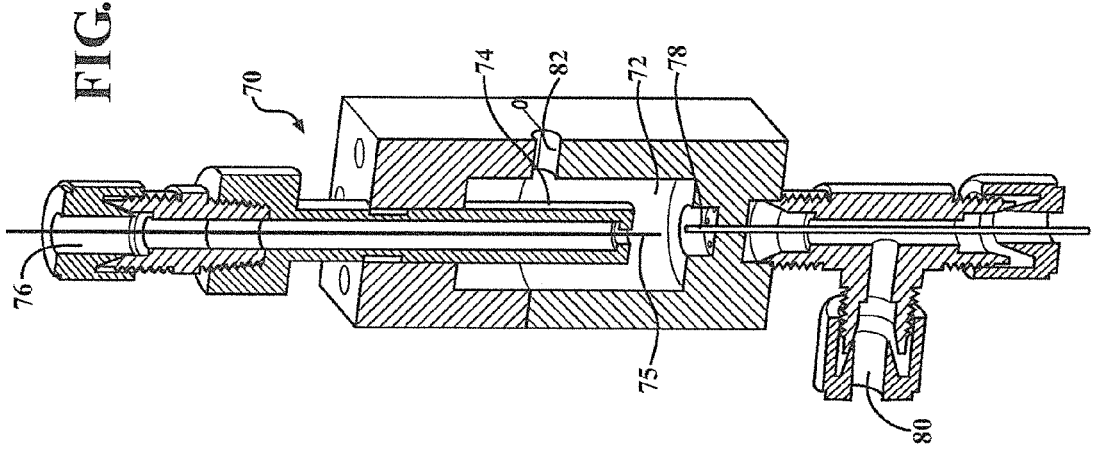
FIG. 3 is a cross sectional view of an alternative embodiment of an apparatus in accordance with the present invention.

FIG. 3 illustrates an alternative housing 70 with a reentrant type cavity 72 defining the collection and analysis area. A reentrant portion 74 of the cavity extends into the collection and analysis area. In this embodiment, the reentrant portion 74 is a hollow generally tubular structure. The aerosol inlet 76 is through the hollow center of the reentrant portion 74. The reentrant portion 74 is grounded and the end of the reentrant portion 74 may serve as a second electrode, in embodiments in which the second electrode is grounded. In the illustrated embodiment, a second electrode 75 extends through the reentrant portion 74 and is spaced from and coaxial with a collection electrode 78. The aerosol outlet 80 extends coaxially about the collection electrode 78, and then turns and exits to the side. A port 82 is provided in the side of the housing for introduction of microwaves. In this embodiment, microwaves may be provided by a coaxial cable from the microwave source. In the illustrated embodiment, the microwave port 82 is above the end of the bullet. Though not shown in this cross sectional view, a window is also provided for collection of light by the spectrometer. This window may be aligned with the end of the collection electrode 78. The embodiments of FIGS. 2 and 3 may additionally include any of the elements discussed for FIG. 1, and any of the embodiments or elements disclosed herein may be combined in various ways that will be clear to those of skill in the art.

The collection electrode is preferably formed of an electrically conducting material, such as metal, with the material chosen so as not to interfere with the spectrographic analysis of the analytes of interest and does not enhance 'matrix effects'. Exemplary materials are tungsten or platinum. The second electrode may be similarly constructed. The bullet and the entire cavity may be metal or other conducting material, and may be grounded.

In another approach, where preconcentration on the electrodes is not needed, aerosol particles could be analyzed on-the-fly, in a microwave plasma produced between two opposing electrodes using any combination of the techniques described above. In this case, the electrodes serve only to create repeatable and robust microwave plasma between the electrodes. The other above-discussed enhancement approaches may additionally or alternatively used with this on-the-fly analysis.

FIG. 4 provides a comparison of two spectra of tungsten (W) obtained using spark plasma (SES) and microwave plasma (CAMPS) respectively. As shown, the signals are much higher for the CAMPS system.

The embodiments disclosed herein may be used in combination with the teachings of co-pending patent applications Ser. Nos. 13/315,344 and 13/315,372, the entire contents of which are incorporated herein by reference.

The herein disclosed embodiments may be altered in various ways without departing from the scope or teaching of the present invention. It is the following claims, including all equivalents, which define the scope of the invention.

The invention claimed is:

1. A method for collecting and analyzing particles of a flow of aerosol, the method comprising:
   providing a housing having an inlet area and an outlet area, the housing further having a collection and analysis area interconnecting the inlet area with the outlet area, a flow path for an aerosol being defined from the inlet area, through the collection and analysis area, and out the outlet area;
   providing a collection electrode having a tip disposed in the flow path in the collection and analysis area;
   providing a second electrode spaced from the collection electrode tip in the collection and analysis area;
   introducing a flow of aerosol along the flow path, wherein the particles of the aerosol passing along the flow path are charged;
   collecting particles of the aerosol on the tip of the collection electrode, the collecting particles step comprising holding the collection electrode at a bias voltage relative to the charged particles such that charged particles collect on the tip of the collection electrode;
   during the collecting particles step, applying a corona current on the tip of the second electrode such that the second electrode creates a high concentration of ions around its tip such that the aerosol particles are charged by the ions for facilitating the collection of the particles on the collection electrode;
   applying a microwave pulse to the collection and analysis area such that a plasma is created on the tip of the collection electrode, thereby ablating and atomizing the collected particles; and
   measuring atomic emissions produced during at least part of the microwave applying step for analysis of the ablated particles.

2. A method for collecting and analyzing particles of a flow of aerosol in accordance with claim 1, further comprising: after the collecting particles step, creating a corona on the tip of the collection electrode and then applying the microwave pulse.

3. A method for collecting and analyzing particles of a flow of aerosol in accordance with claim 1, wherein the second electrode and the collection electrode are coaxially aligned.

4. A method for collecting and analyzing particles of a flow of aerosol in accordance with claim 1, wherein: during the collecting particles step, holding the second electrode at a second voltage relative to the bias voltage so as to create an electrical field forcing charged aerosol particles toward the tip of the collection electrode.

5. A method for collecting and analyzing particles of a flow of aerosol in accordance with claim 1, further comprising:
   providing a corona electrode adjacent the collection electrode; and
   after the collecting particles step, creating a corona using the corona electrode and then applying the microwave pulse, wherein the corona using the corona electrode enhances the concentrations of the charged particles in the vicinity of the collection electrode to allow efficient reproducible coupling of the microwave.

6. A method for collecting and analyzing particles of a flow of aerosol in accordance with claim 1, further comprising:
   providing a second electrode spaced from the collection electrode tip so as to define a spark gap in the collection and analysis area; and
   after the collecting particles step, creating a pulsed high-voltage spark or arc across the spark gap to at least partially ablate the particles on the collection electrode and then applying the microwave pulse.

7. A method for collecting and analyzing particles of a flow of aerosol in accordance with claim 1, further comprising:
   providing a laser source; and
   after the collecting particles step, at least partially ablating the particles on the collection electrode using the laser and then applying the microwave pulse.

8. A method for collecting and analyzing particles of a flow of aerosol in accordance with claim 1, further comprising:
   providing a source of UV or soft X-ray photoionization or a small radioactive alpha and beta sources to provide ionized particles; and
   after the collecting particles step, inducing ionization of air in the vicinity of the collection electrode using the source of UV or soft X-ray photoionization and then applying the microwave pulse.

9. A method for collecting and analyzing particles of a flow of aerosol in accordance with claim 1, further comprising:
   providing a hollow reentrant portion extending into the collection and analysis area; and
   introducing the flow of aerosol through the hollow reentrant portion.

10. A method for collecting and analyzing particles of a flow of aerosol in accordance with claim 9, wherein:
    the reentrant portion is coaxial with the collection electrode.

11. A method for collecting and analyzing particles of a flow of aerosol in accordance with claim 1, further comprising:
    providing a microwave generator and a waveguide or coaxial cable; and
    then applying a microwave pulse step comprises generating a microwave pulse with the microwave generator and guiding the microwave pulse to the collection and analysis area through the waveguide or cable.

12. A method for collecting and analyzing particles of a flow of aerosol in accordance with claim 1, further comprising:
    providing a spectrometer;
    wherein the collecting atomic emissions step comprises collecting atomic emissions with the spectrometer.

13. A method for collecting and analyzing particles of a flow of aerosol in accordance with claim 1, further comprising:
    providing an aerosol charger; and
    charging the particles of the aerosol prior to introducing the flow of aerosol to the collection and analysis area.

14. A method for collecting and analyzing particles of a flow of aerosol in accordance with claim 1, wherein:
    the housing is a reentrant type cavity.

* * * * *